(12) United States Patent
Sato

(10) Patent No.: US 8,262,558 B2
(45) Date of Patent: Sep. 11, 2012

(54) TREATMENT TOOL

(75) Inventor: Kazuya Sato, Hirosaki (JP)

(73) Assignee: Olympus Medical Systems Corp, Tokyo (JP)

( * ) Notice: Subject to any disclaimer, the term of this patent is extended or adjusted under 35 U.S.C. 154(b) by 370 days.

(21) Appl. No.: 12/504,750

(22) Filed: Jul. 17, 2009

(65) Prior Publication Data

US 2010/0010295 A1  Jan. 14, 2010

Related U.S. Application Data

(63) Continuation of application No. PCT/JP2008/050428, filed on Jan. 16, 2008.

(30) Foreign Application Priority Data

Jan. 19, 2007  (JP) ................................ 2007-010002

(51) Int. Cl.
*A61B 1/00* (2006.01)

(52) U.S. Cl. .......................... 600/104; 600/101; 600/125

(58) Field of Classification Search .......... 600/101–112, 600/119, 121–123, 125, 130, 131; 606/1
See application file for complete search history.

(56) References Cited

U.S. PATENT DOCUMENTS

2005/0245875 A1  11/2005  Restelli et al.

FOREIGN PATENT DOCUMENTS

| JP | 57-126201 | 8/1982 |
| JP | H05-245101 | 9/1993 |
| JP | H06-81544 | 11/1994 |
| JP | 10-85331 | 4/1998 |
| JP | 2001-58006 | 3/2001 |
| JP | 2005-534436 A | 11/2005 |
| JP | 2007-260218 | 10/2007 |
| WO | WO 02/36179 A2 | 5/2002 |

OTHER PUBLICATIONS

Extended Supplementary European Search Report dated Feb. 1, 2010.
International Search Report dated Mar. 18, 2008 together with English language translation.

*Primary Examiner* — Ahmed Farah
(74) *Attorney, Agent, or Firm* — Scully, Scott, Murphy & Presser, P.C.

(57) ABSTRACT

This treatment tool having: an inserted part that can be inserted and passed through an endoscope, in which a treatment part for carrying out a specific treatment on a tissue is provided to the distal end of the inserted part which is passed through the endoscope and disposed inside the body. The treatment part being provided to the inserted part so as to be freely projecting and retracting; and provided with: an operator portion at the base end portion of the inserted part which is pulled out from the endoscope, for manipulating the projection and retraction of the treatment part.

4 Claims, 13 Drawing Sheets

TREATMENT TOOL

TECHNICAL FIELD

The present invention relates to a treatment tool that is employed following insertion into an endoscope.

Priority is claimed on Japanese Patent Application No. 2007-10002, filed Jan. 19, 2007, the content of which is incorporated herein by reference.

BACKGROUND ART

Endoscope treatment tools which can be inserted into the channel of an endoscope are employed when performing per os treatments using an endoscope. The endoscope treatment tool has a flexible, long and narrow inserted part. A treatment part for carrying out the treatment is provided on the distal end of the inserted part which is inserted into the body. An operator portion for manipulating the treatment part is provided to the base end of the inserted part, which is pulled out on the hand-held side.

An injection syringe may be cited here as one example of an endoscope treatment tool and is used when injecting and infusing a medicinal liquid into a tissue. This injection syringe is a treatment part in which a hollow needle is passed in a freely advancing and retreating manner through a sheath, which serves as the inserted part, with the distal end of the hollow needle piercing the tissue. The operator portion includes a pipe-shaped operator portion main body which is fixed in place to the base end of the sheath, and a base which is attached in a freely advancing and retreating manner to the operator portion main body and is connected to the hollow needle. This type of injection syringe is introduced into the body in an arrangement in which the distal end of the hollow needle is housed within the sheath. When piercing the tissue, the base is pushed in relative to the operator portion main body, causing the distal end of the hollow needle to be projected out from the sheath.

The design of an operator portion for switching between projecting out and retracting back the hollow needle is disclosed, for example, in Patent Reference No. 1. In this operator portion, a vertically directed groove is provided to the operator portion main body, with the ends of the groove forming stopping seats which are expanded in an approximately circular shape. An operator tube which is inserted into the operator portion main body is connected to the base, and an elastic ligulate section extending in the vertical direction is provided to the operator tube. A pin is provided to the free end of the elastic ligulate section. This pin has a two-step design with differing diameters. The large diameter base portion is larger than the width of the groove on the operator portion main body side, but is smaller than the diameter of the stopping seats. The small diameter distal end portion is smaller than the width of the groove. The operator tube is inserted into the operator portion main body and is biased by means of a spring in the direction of retreating of the hollow needle.

When assembling the injection syringe, the operator tube is inserted into the operator portion main body until the pin reaches the front stopping seat. The elastic ligulate section reverts to its original state, and the pin enters the front stopping seat. At this time, the distal end of the hollow needle is located at its operating position, projecting out from the sheath. Once the treatment is concluded, the operator manually pushes in the pin. The compressed spring reverts to its original state and the operator tube and the base are pushed back. The distal end portion of the pin moves while being guided in the groove. Once the rear stopping seat is reached, the elastic ligulate section reverts to its original state, and the pin enters the rear stopping seat, causing the operator tube and base to stop. At this position, the distal end of the hollow needle is housed inside the sheath.

[Patent Document 1]
  Published Japanese translation No. 2005-534436 of PCT International Publication

DISCLOSURE OF THE INVENTION

Problems to be Solved by the Invention

However, in an operator portion such as described above, the action of pushing in a button when projecting out or retracting back the hollow needle is necessary. In particular, when advancing the hollow needle, the base must be advanced while pushing in the button, making the operation complicated. Further, the device design is complicated since a spring or a flat spring-type elastic ligulate section is used.

The present invention was conceived in view of the above-described circumstances and has as its objective enabling easy execution of the advancing and retreating operations of a treatment part such as a hollow needle, by means of a simple design.

Means to Solve the Problem

In order to resolve the above problems, the present invention is a treatment tool having:

an inserted part that can be inserted and passed through an endoscope, in which a treatment part for carrying out a specific treatment on a tissue is provided to the distal end of the inserted part which is passed through the endoscope and disposed inside the body, the treatment part being provided to the inserted part so as to be freely projecting and retracting; and provided with: an operator portion at the base end portion of the inserted part which is pulled out from the endoscope, for manipulating the projection and retraction of the treatment part. The operator portion is provided with an operator portion main body which is fixed to the sheath of the inserted part; and an operator tube which is inserted in a freely advancing and retreating manner into a hole formed in the operator portion main body, and in which a base is provided that communicates with the treatment part. Expanded diameter sections which increase the inner diameter are formed to the hole of the operator portion main body at two sites along the advancing/retreating direction of the operator tube, the expanded diameter section on the base end side being formed corresponding to the position at which the treatment part is housed in the sheath, and the expanded diameter section on the distal end side being formed corresponding to the position at which the treatment part is projected out from the sheath. Locking parts which undergo deformation in the radial direction to engage with the expanded diameter sections are provided to the operator tube; and an inclined surface which inclines with respect to the advancing/retreating direction is provided to at least one of the expanded diameter sections or the locking parts.

When the expanded diameter section engages with the locking parts in this treatment part, the treatment part is locked at that position. When the treatment part is moved, the operator tube is moved. In this case, when the inclined surface which is provided to the locking parts or the expanded diameter sections is formed with an inclination that deforms the locking parts inward in the radial direction, the engagement is released and movement becomes possible. When the inclined surface which is provided to the locking parts or the expanded diameter sections is formed with an inclination that is opposite that which deforms the locking parts inward in the radial direction, the engagement is maintained and movement is not possible.

In the above treatment tool, it is acceptable to design the expanded diameter section that is formed on the distal end side so that the inclined surface is formed with an orientation which applies pushing pressure so as to close the locking parts when the operator tube is retreated, and to design the expanded diameter section that is formed on the base end side so that the inclined surface is formed with an orientation which applies pushing pressure so as to close the locking parts when the operator tube is advanced.

In this treatment tool, the inclined surface in the expanded diameter section on the distal end side functions to release engagement in the direction for housing a treatment part that has been projected outward. The inclined surface in the expanded diameter section on the base end side functions to release engagement in the direction for projecting out the treatment part from the housed state.

In the above-described treatment tool, the inclined surface may be formed to the expanded diameter section formed on the base end side with an orientation that prevents its pulling out by engaging with locking parts in the direction for pulling out the operator tube further.

In this treatment tool, when an attempt is made to pull back the operator tube further at a time when the locking parts are engaged with the expanded diameter sections on the base end side, the inclined surface functions to check movement of the locking parts inward in the radial direction, and functions to prevent the operator tube from being pulled out of the operator portion main body.

In this treatment tool, an inclined surface may be formed on the distal end portion of the locking parts so as to reduce the outer profile toward the axial line of the operator tube in the advancing direction, and the inclined surface may be formed on the base end portion of the locking parts so as to reduce the outer profile toward the axial line of the operator tube in the retreating direction.

In this treatment tool, the inclined surface on the base end side of the locking parts functions to release the engagement in the direction for housing the treatment tool which has been projected outward, and the inclined surface on the distal end side of the locking parts functions to release the engagement in the direction for projecting out the treatment part out from the housed state.

In this treatment tool, the locking parts may have projecting parts capable of engaging with the expanded diameter section, and may have an inclined end surface on the base end side of the projecting parts which deforms the locking parts in the direction of reduced diameter during retreat of the operator tube, and an inclined surface provided to a position deviated in the advancing/retreating direction with respect to the end surface which is inclined in the direction opposite the aforementioned inclined surface; and the expanded diameter section on the base end side of the operator portion main body may have a surface which engages with the inclined surface in the direction for further retreating the operator tube.

In this treatment tool, when the operator tube is retreated from the expanded diameter section on the distal end side, the end surface and the distal end side expanded diameter section work cooperatively to deform the locking parts in the direction of reduced diameter to enable movement of the operator tube. If the operator tube is pulled further, then the inclined surface on the expanded diameter section on the base end side engages with the surface on the expanded diameter section side. As a result, the operator tube is prevented from being pulled out.

In this treatment tool, the base end side center portion of the projecting part of the locking parts extends in the advancing/retreating direction, and the end surface is formed to this center portion. The inclined surfaces are disposed to either side with the center portion therebetween. A slit capable of receiving the center portion of this projecting part may be formed to the base end side expanded diameter section.

In this treatment tool, the end surface which is used when retreating the operator tube from the expanded diameter section on the distal end side projects out toward the base end side. When the operator tube is pulled toward the expanded diameter section on the base end side, the outwardly projecting center portion advances into the slit in the expanded diameter section on the base end side, preventing interference between the expanded diameter section and the projecting part.

EFFECTS OF THE INVENTION

In the present invention, an inclined surface for controlling the engagement and release of engagement with the operator portion main body by advancing/retreating action of the operator tube is provided to a design in which the treatment part is made to project out or retract back by advancing or retreating the operator tube with respect to the operator portion main body. As a result, it is possible to carry out the projection, retraction or locking into position of the treatment part by simply advancing or retreating the operator tube. Thus, the operation of the treatment part becomes simple. Moreover, the device design for the operator portion can be simplified.

DESCRIPTION OF THE SYMBOLS

1 ... injection syringe (treatment tool), 2 ... inserted part, 3 ... sheath, 4 ... hollow needle (treatment part), 5, 71 ... operator portion, 21, 72 ... operator portion main body, 22, 73 ... operator tube, 25 ... hole, 41, 92 ... base, 31, 61, 81 ... first expanded diameter section, 32, 62, 82 ... second expanded diameter section, 33A, 33B, 35A, 35B, 52A, 66A, 66B, 86, 96A, 96B ... inclined surface, 51, 93 ... locking part, 95 ... projecting part, 96 ... projecting part main body, 97 ... edge part, 97A ... end surface

BEST MODE FOR CARRYING OUT THE INVENTION

Embodiments of the present invention will now be explained with reference to the figures. The same numeric symbol will be applied to compositional elements that are the same throughout the various embodiments, and a redundant explanation thereof will be omitted.
(First Embodiment)

Figure 1:
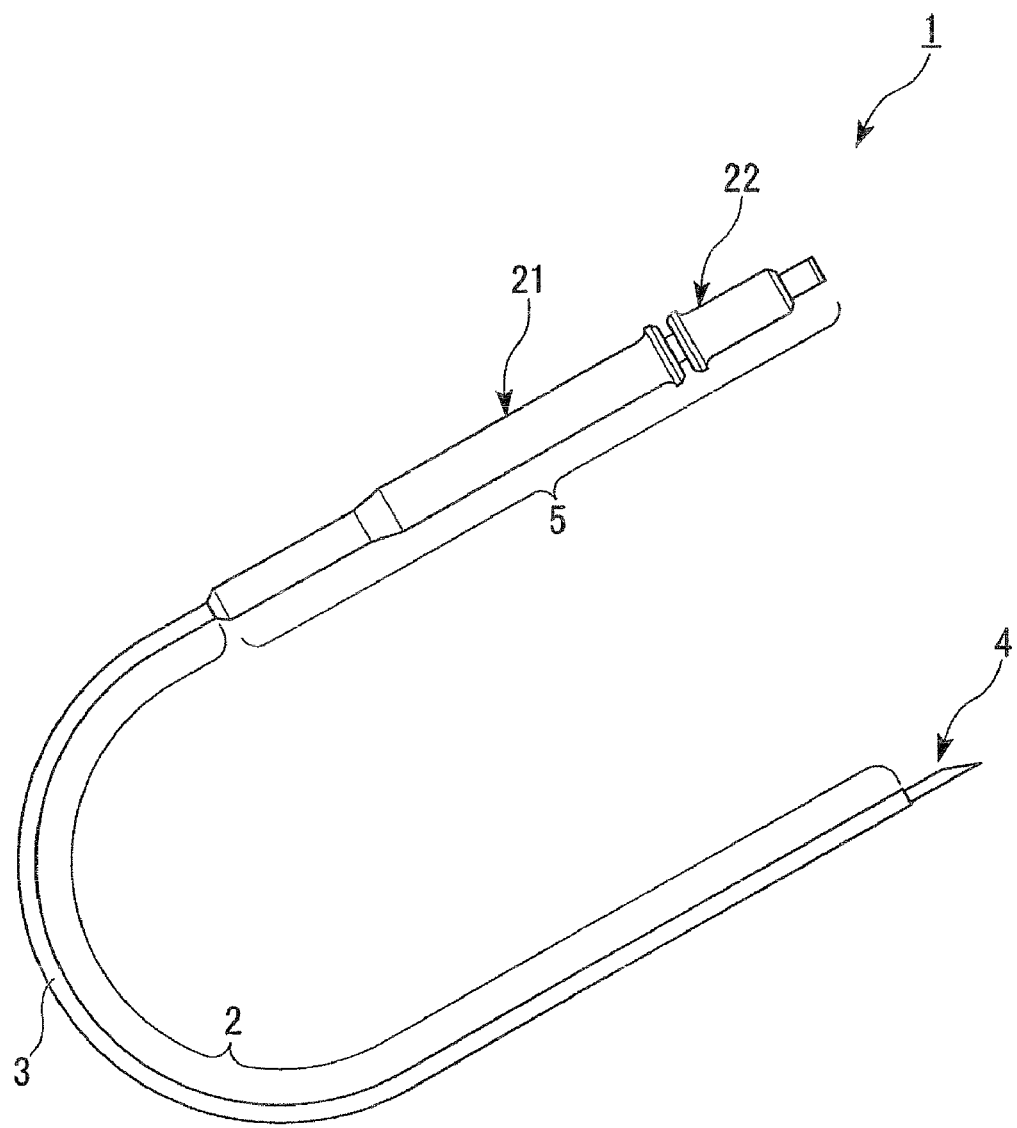
FIG. 1 is a sketch view of the injection syringe which is one example of the treatment tool according to an embodiment of the present invention.

The overall structure of the injection syringe, which is the endoscope treatment tool, is shown in FIG. 1. The injection syringe 1 has a design in which a hollow needle 4, which serves as the treatment part, is provided in a freely projecting and retracting manner to the distal end of a long and narrow sheath 3 which serves as the inserted part 2. The operator portion 5 is attached to the base end portion of the sheath 3.

Figure 2:
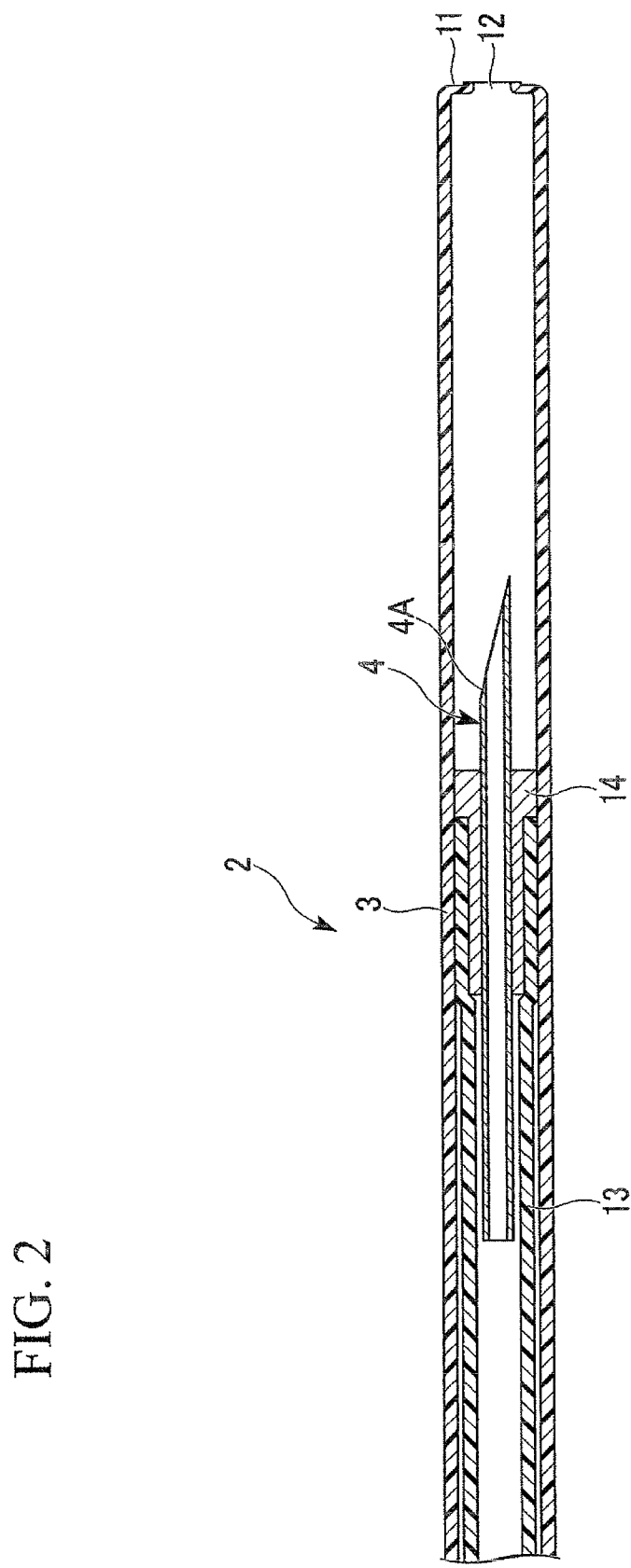
FIG. 2 is an expanded cross-sectional view of the distal end portion of the injection syringe, showing an arrangement in which the hollow needle is housed inside the sheath.

A resin tube is employed for the sheath 3. As shown in cross-section in FIG. 2, in which the hollow needle 4 is in the housed state, the distal end portion of the sheath 3 forms a stopper 11 in which the diameter of the opening is reduced. The diameter of the opening 12 formed by stopper 11 permits insertion and passage of the hollow needle 4, but is of a size which offers sliding resistance such that a certain amount of force is necessary for insertion.

The hollow needle 4 is fixed to the distal end of a flexible liquid relaying tube 13 by press fitting via a joint 14. The hollow needle 4 is formed from a rigid material, with the distal end thereof forming a sharp end 4A. The outer diameter of the hollow needle 4 is smaller than the inner diameter of the liquid relaying tube 13. The liquid relaying tube 13 is formed of a soft resin such as PFA (tetrafluoro-perfluoroalkyl vinyl ether resin, for example. The liquid relaying tube 13 passes into the sheath 3 in a freely advancing and retreating manner, with the base end portion thereof pulled into the operator portion 5 which is fixed to the sheath 3.

Figure 3:
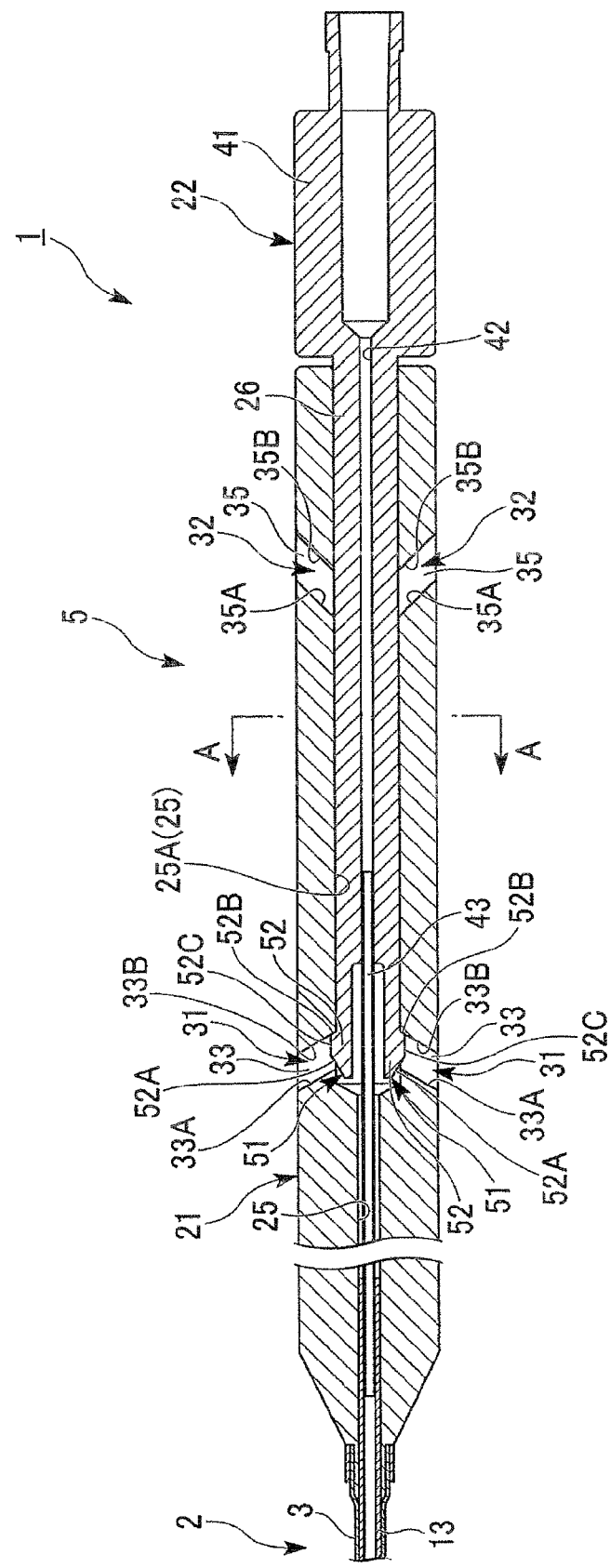
FIG. 3 is a cross-sectional view showing the structure of the operator portion.
Figure 4:
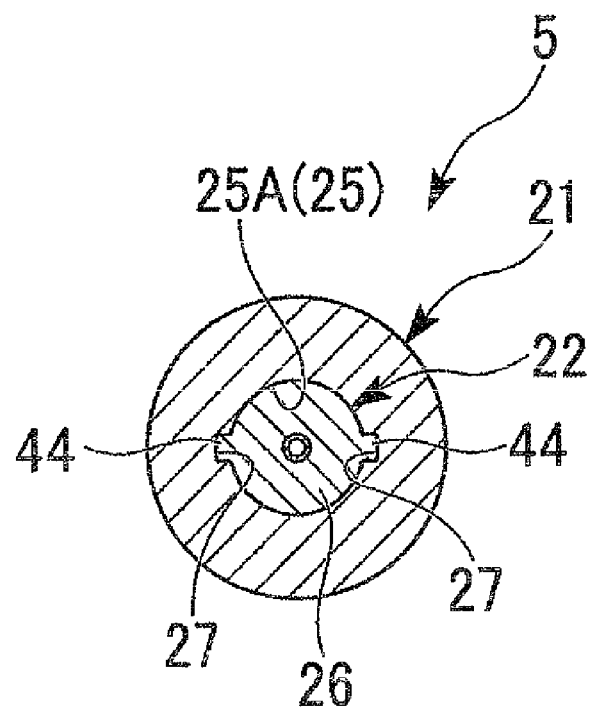
FIG. 4 is a cross-sectional view along the line A-A in FIG. 3.

As shown in FIGS. 1 and 3, the operator portion 5 has an operator portion main body 21 which is inserted into and fixed to the base end portion of the sheath 3, and an operator tube 22 which is inserted into the operator portion main body 21 in a freely advancing and retreating manner. A hole 25 is formed in the operator portion main body 21, penetrating through the direction of its length (axial direction). A liquid relaying tube 13 is inserted into this hole 25. The base end side of the hole 25 has an expanded diameter relative to the distal end side, and the tube portion 26 of the operator tube 22 is inserted into the widened diameter hole 25A. As shown in FIG. 4, two key grooves 27 are formed extending in the length direction in expanded diameter hole 25A. The number and position of key groove 27 are not restricted to those shown in the figures.

Expanded diameter sections 31, 32, in which the inner diameter is increased, are formed to the distal end side and base end side respectively of the expanded diameter hole 25A, so as to avoid the key grooves 27. The pair of first expanded diameter sections 31 on the distal end side are provided symmetrically on either side of the hole 25A. These are each formed from holes 33 which are provided from the outer periphery of the operator portion main body 21 toward the expanded diameter hole 25A. These holes 33 are provided at an inclination so that the inner peripheral side opening is formed on the base end side relative to the outer peripheral side opening. As a result, the wall surface on the distal end side of the hole 33 forms an inclined surface 33A which forms an obtuse angle with the direction toward the distal end side of the axial line. The wall surface of the base end side of the hole 33 forms an inclined surface 33B which forms an acute angle with the direction toward the distal end side of the axial line.

A pair of second expanded diameter sections 32 on the base end side are provided symmetrically with the hole 25A therebetween. These are each formed from holes 35 which are provided from the outer periphery of the operator portion main body 21 toward the expanded diameter hole 25A. These holes 35 are provided at an inclination so that the opening on the inner peripheral side is formed on the distal end side relative to the opening of the outer peripheral side. As a result, the wall surface on the distal end side of the hole 35 forms inclined surface 35A which forms an obtuse angle with the direction toward the distal end side of the axial line. The wall surface on the base end side of the hole 35 forms an inclined surface 35B which forms an acute angle with the direction toward the distal end side of the axial line.

In the operator tube 22, the base 41 is formed in a unitary manner to the base end of the tube portion 26 which can be inserted into the hole 25A. A through hole 42 is provided to the operator tube 22, from the base 41 to the distal end of the tube portion 26. A rigid pipe 43 is fixed to the distal end portion of the through hole 42 by press fitting. This pipe 43 is advanced inside the hole 25 of the operator portion main body 21 and is connected to the liquid relaying tube 13.

As shown in FIG. 4, two keys 44 are provided projecting out from the outer periphery of the tube portion 26. The keys 44 are formed to align with the position of formation of the key grooves 27 on the operator portion main body 21 side. Rotation can be stopped by inserting the keys 44 into the key grooves 27.

As shown in FIG. 3, a pair of locking parts 51 is formed to the distal end of the operator tube 22 so as to grip pipe 43 therebetween. The paired locking parts 51 are a component that is formed to permit elastic deformation due to introduction of a slit at the distal end of the tube portion 26. A projecting part 52 is provided in the radial direction to the outside of the distal end portion, which serves as a free end, of the locking parts 51. This projecting part 52 has an inclined surface 52A which is cut with an inclination so that the distal end is directed toward the center. The base end side of the projecting part 52 forms a flat surface 52B roughly lying along the radial direction. When external force is not being applied, the distance between the pair of outer surfaces 52C of projecting part 52 is greater than the diameter of the hole 25A.

The locking parts 51 and the expanded diameter sections 31, 32 are formed so that when the projecting parts 52 of the locking parts 51 are aligned with the first expanded diameter section 31, the hollow needle 4 projects out from the sheath 3 and is located at the operating position which insertion into the tissue is possible. Further, the locking parts 51 and the expanded diameter sections 31, 32 are formed so that when the projecting parts 52 of the locking parts 51 are aligned with the second expanded diameter section 32, the hollow needle 4 is located at the housing position at which the hollow needle 4 is completely pulled into the sheath 3.

The operation of the injection syringe will now be explained.

Figure 5:
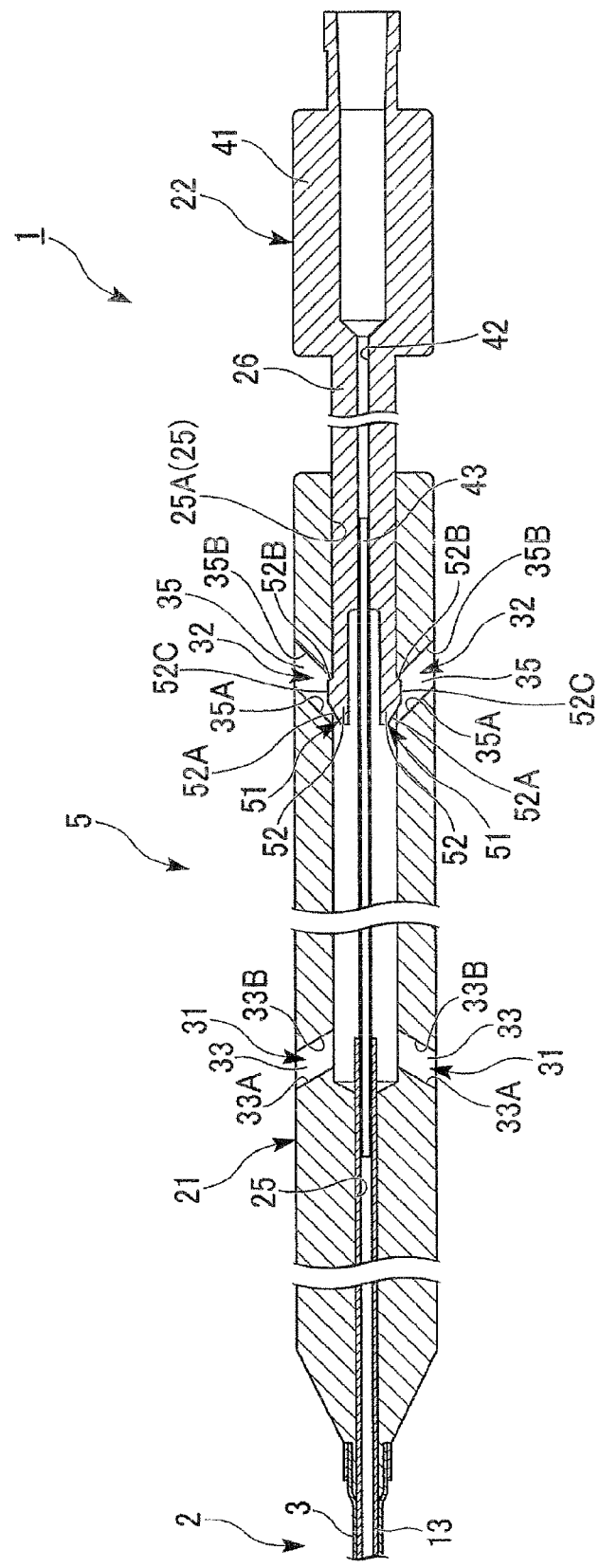
FIG. 5 is a cross-sectional view for explaining the disposition after the operator tube has been retracted and the hollow needle has been housed inside the sheath.

An endoscope, not shown in the figures, is inserted via the patient's mouth or other such orifice, and the targeted treatment site is approached while using the image pick-up device of the endoscope for confirmation. An injection syringe 1 is inserted into the working channel of the endoscope and the distal end of the sheath 3 of the inserted part 2 is guided inside the body. As shown in FIG. 5, in the initial state in operator portion 5, the projecting parts 52 of the locking parts 51 are engaged by the second expanded diameter section 32, and the hollow needle 4 is housed inside the sheath 3 as shown in the FIG. 2. At this position, the surface 52B of the projecting part 52 comes into contact with the acute angle inclined surface 35B of the expanded diameter section 32. As a result, it is not possible to pull out the operator tube 22 any further.

When projecting out the hollow needle 4, the base 41 is gripped and the operator tube 22 is pushed into the operator portion main body 21. The pair of locking parts 51 are pushed in the closing direction by the inclined surface 32A on the distal end side of the second expanded diameter section 32. The distance between the outer surfaces 52C of the projecting parts 52 becomes smaller than the diameter of the hole 25A. As a result, the pair of locking parts 51 can advance inside the hole 25A. When the operator tube 22 is pushed in, the hollow needle 4, which is connected to operator tube 22 via pipe 43 and liquid relay tube 13, is advanced.

The diameter of the hole 25A is roughly constant until the first expanded diameter section 31, thus the operator tube 22 advances smoothly and the hollow needle 4 begins to project out from the sheath 3. Once the projecting parts 52 on the pair of locking parts 51 reaches the first expanded diameter section 31, the locking parts 51 revert to their original state and open, so that the locking parts 51 are housed inside the first expanded diameter section 31. When the operator tube 22 is located at this position, the hollow needle 4 is projected out from the sheath 3 on the distal end side and engages in the opening 12 on the distal end of the sheath 3.

When an attempt is made to further advance the operator tube 22 at this point, the inclined surface 52A on the distal end of the projecting part 52 comes into contact with the inclined surface 33A of the first expanded diameter section 31. The inclined surface 33A is inclined in a direction which causes interference without applying pressure on the locking parts 51 in the reduced diameter direction. Thus, the operator tube 22 cannot advance beyond this point. Conversely, if an attempt is made to retreat the operator tube 22 by pulling using a relatively mild force, then the surface 52B on the base end side of the projecting part 52 comes into contact and interferes with the inclined surface 33B at the first expanded diameter part section 31. In other words, the locking parts 51 engage with the first expanded diameter section 31, and the position of the hollow needle 4 is locked. Accordingly, the hollow needle 4 will pierce and penetrate the tissue if the main body of the injection syringe 1 is advanced.

When the hollow needle 4 pierces the tissue, a medicinal liquid, saline or other such liquid is delivered from a syringe attached to the base 41. The liquid passes through the liquid relay tube 13 and is injected into the tissue via the hollow needle 4. Once the treatment is completed, the injection syringe 1 is retreated and the hollow needle 4 is pulled out from the tissue.

When housing the hollow needle 4 in the sheath 3, the operator tube 22 is pulled and retreated with a force stronger than that applied during piercing. The projecting parts 52 of the locking parts 51 are pushed by the inclined surface 33B of the first expanded diameter section 31, and the pair of locking parts 51 close. As a result, the operator tube 22 can be retreated. The engaging force between the inclined surface 33B of the first expanded diameter section 31 and the projecting part 52 stops the movement of the operator tube 22 when piercing the tissue with the hollow needle 4. When the base 41 is manually pulled, a contour is set so as to cause deformation of the pair of locking parts 51.

When the projecting parts 52 reach the second expanded diameter section 32 during the process of retreating the operator tube 22, the pair of locking parts 51 revert to their original state and are caught in the operator portion main body 21. When stopping at this position, the hollow needle 4 is housed inside the sheath 3. Note that the inclined surface 35B on the base end side of the second expanded diameter section 32 interferes with the locking parts 51 and prevents its pulling out in the direction of retreat of the operator tube 22. Accordingly, the operator tube 22 does not fall out during ordinary operation.

In this embodiment, two expanded diameter sections 31, 32 are provided in the advancing/retracting direction of the hollow needle 4, and a tapered surface is formed to the expanded diameter sections 31, 32. As a result, by simply advancing or retreating the operator tube 22, it is possible to deform the projecting parts 52 on the operator tube 22 side. Thus, operation is facilitated by means of a simple structure. The respective expanded diameter sections 31, 32 are formed so as to correspond to the operating position at which hollow needle 4 projects out and to the housing position at which the hollow needle 4 is completely housed inside the sheath 3. As a result, projection or retraction of the hollow needle 4 can be controlled by simply moving the operator tube 22 to the position at which it is engaged and stopped.

In the conventional art, injection syringes of the type in which the base is pushed or screwed into the operator portion main body and the hollow needle is fixed at the operating position ultimately require application of considerable force for the pushing and screwing in action. In contrast, this injection syringe 1 does not require a large amount of force to be finally applied, so that the operation is easy. Further, the situation is eliminated in which the required force for fixing the hollow needle 4 in place at the operating position is not sufficient.

(Second Embodiment)

This embodiment is characterized in the provision of an inclined surface to the base side only.

Figure 6:
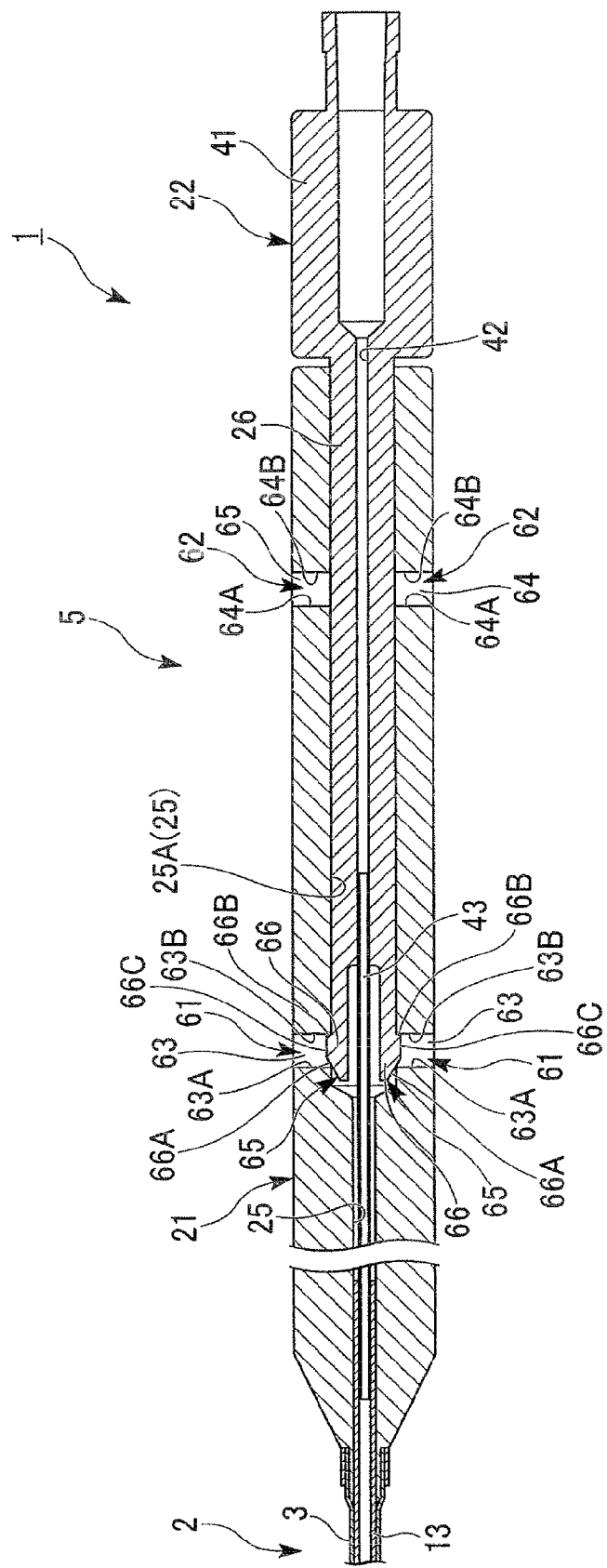
FIG. 6 is a cross-sectional view showing another embodiment of the operator portion of the injection syringe.
Figure 7:
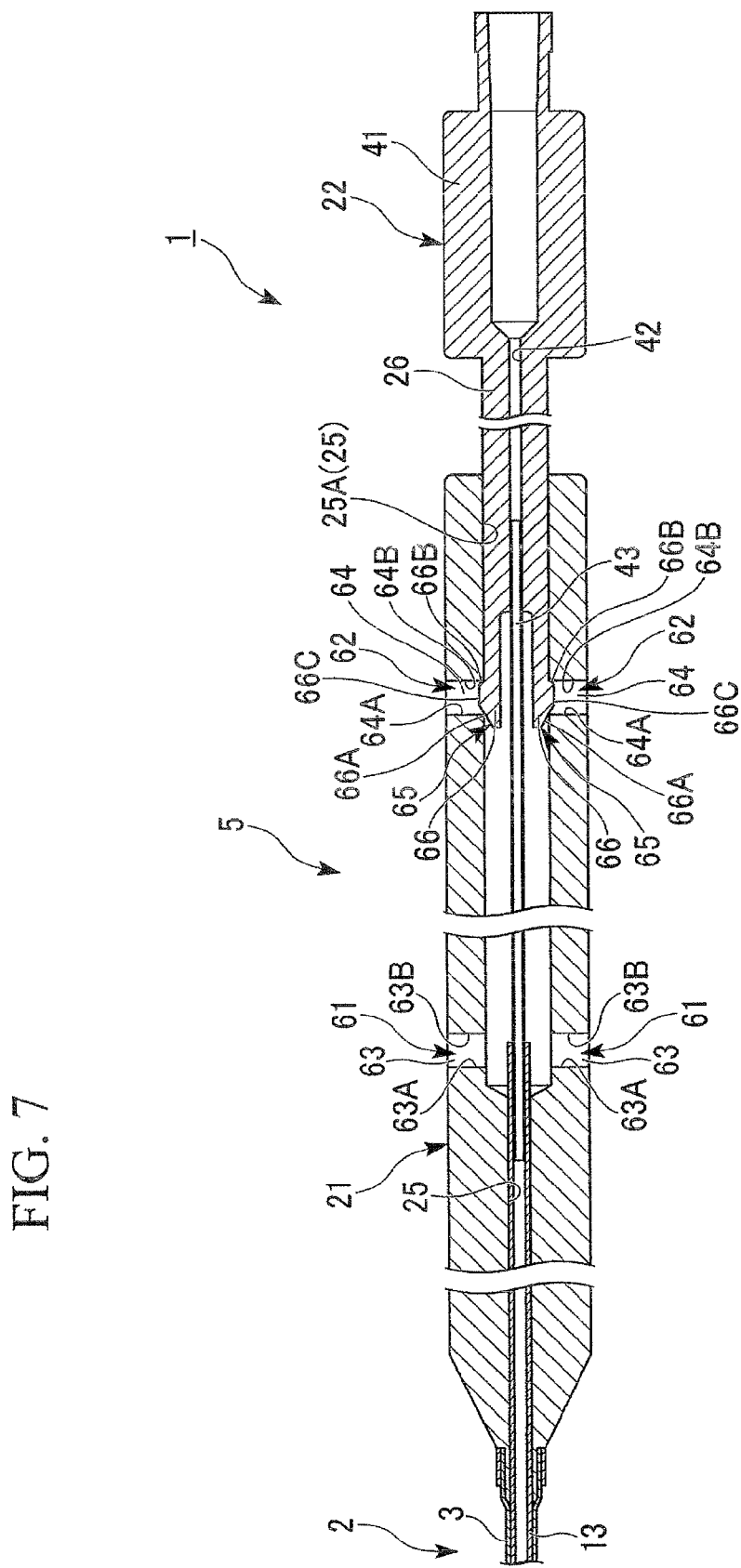
FIG. 7 is a cross-sectional view for explaining the disposition after the operator tube has been retreated and the hollow needle has been housed inside the sheath in the operator portion in FIG. 6.

As shown in FIG. 6, respective pairs of a first expanded diameter section 61 and a second expanded diameter section 62 are provided to the operator portion main body 21. The first expanded diameter section 61 is formed corresponding to the operating position at which the hollow needle 4 is projected out from the sheath 3. The second expanded diameter section 62 is formed corresponding to the housing position at which the hollow needle 4 is pulled back into the sheath 3. These expanded diameter sections 61, 62 includes holes 63, 64 which penetrate from the outer peripheral surface of the operator portion main body 21 to the hole 25, in a direction which is perpendicular to the axis. Accordingly, the wall surfaces 63A, 64A on the distal end side and the wall surfaces 63B, 64B on the base end side of these holes 63, 64 serve as surfaces which intersect respectively with the axis.

A pair of locking parts 65 are provided to the distal end of the operator tube 22 to which base 41 is provided. Inclined surfaces 66A, 66B are formed on the distal end side and the base end side respectively of the projecting parts 66 of the locking parts 65. The inclined surface 66A is inclined so as to close in the direction approaching the distal end side, i.e., so as to decrease its outer profile in the direction of advance toward the axis of the operator tube 22. The inclined surface 66B is inclined so as to close when directed toward the base 41, i.e., is inclined so as to decrease its outer profile when directed toward the axis of the operator tube 22 in the retreating direction.

When housing the hollow needle 4 in the sheath 3, the locking parts 65 engage and are stopped by the second expanded diameter section 62. When moving the hollow needle 4 to the operating position, the base 41 is gripped and the operator tube 22 is advanced. The inclined surfaces 66A on the distal end side of the projecting parts 66 of the locking parts 65 are pushed by the wall surfaces 64A on the distal end side of the second expanded diameter section 62, and the locking parts 65 are pushed inward in the radial direction. When the distance between the outer surfaces 66C of the projecting parts 66 gradually decreases to roughly equal the diameter of the hole 25A, the operator tube 22 advances into the hole 25A. The diameter of the hole 25A is roughly constant until the first expanded diameter section 61, so that the operator tube 22 advances smoothly, and the hollow needle 4 begins to project out from the sheath 3. Once the locking parts 65 reach the first expanded diameter section 61, the locking parts 65 revert to the original state, and the projecting parts 66 advance into the first expanded diameter section 61 where they engages and are stopped. When the operator tube 22 is at this position, the hollow needle 4 projects out from the sheath 3 on the distal end side and engages in the opening 12 on the distal end of the sheath 3.

When pulling back the hollow needle 4, the base 41 is gripped and the operator tube 22 is retreated. The inclined surfaces 66B on the base end side of the projecting parts 66 are pushed by the wall surfaces 63B on the base end side of the first expanded diameter section 61, and the locking parts 65 are pushed inward in the radial direction. The distance between the locking parts 65 gradually decreases to roughly equal the diameter of the hole 25A. The operator tube 22 retreats into the hole 25A, and the hollow needle 4 is pulled into the sheath 3. Once the locking parts 65 reach the second expanded diameter section 62, the locking parts 65 revert to their original state, and the projecting parts 66 advance into the second expanded diameter section 62 where they engage and are stopped. At this point, the hollow needle 4 is completely housed within the sheath 3.

In this embodiment, the holes 63,64 forming the expanded diameter sections 61,62 intersect with the axis, so that production is simple. Other effects are the same as those obtained with the first embodiment.

(Third Embodiment)

Figure 8:
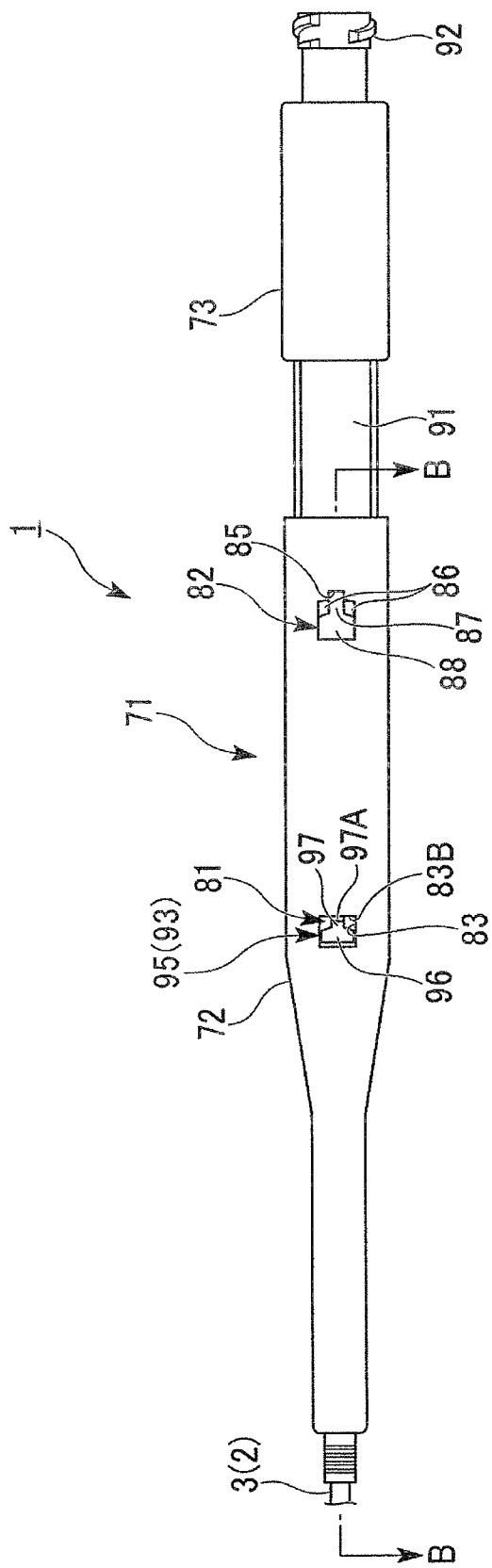
FIG. 8 is a perspective view showing another embodiment of the operator portion of the injection syringe.

FIG. 8 shows the structure of the operator portion 71 of the injection syringe 1 according to this embodiment. Note that the inserted part 2 and the hollow needle 4 are equivalent to those described in the first embodiment.

The operator portion 71 has an operator portion main body 72 fixed in place to the sheath 3 and an operator tube 73 which is inserted in a freely advancing/retreating manner to the operator portion main body 72. As shown by the cross-sectional form in FIG. 9, the key groove 27 is formed to hole 25A of the operator portion main body 72, along the longitudinal direction thereof, and prevents rotation of the operator tube 73. Further, the first expanded diameter section 81 is formed to the distal end side of the operator portion main body 72 and the second expanded diameter section 82 is formed to the base end side of the operator portion main body 72 so as to widen the diameter of the hole 25A, and at positions which avoid the respective key grooves 27.

A pair of first expanded diameter sections 81 are formed on the distal end side, with hole 25A therebetween. These expanded diameter sections 81 includes through holes 83 which penetrate from the operator portion main body 72 to the hole 25A. The through holes 83 form vertical walls in which the wall surface 83A on the distal end side and the wall surface 83B on the base end side approximately intersect with operator portion main body 72 in the longitudinal direction. As shown in FIG. 8, the first expanded diameter section 81 is approximately rectangular when viewed perpendicular to the longitudinal direction of the operator portion main body 72.

Figure 9:
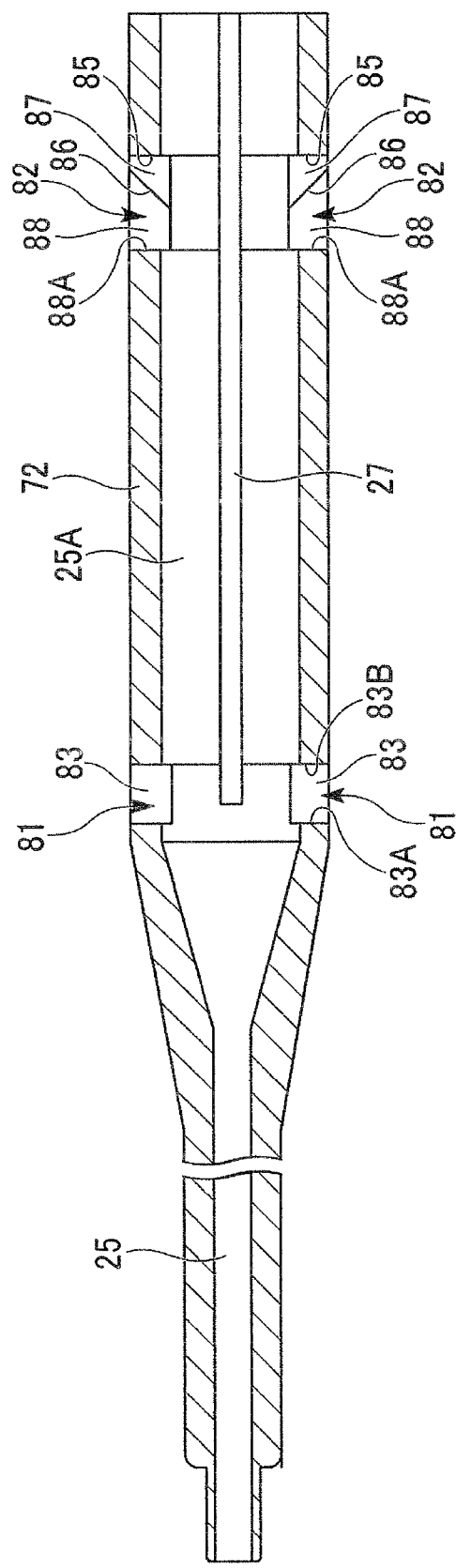
FIG. 9 is a cross-sectional view along the line B-B in FIG. 8.

The second expanded diameter section 82 on the base end side is approximately rectangular as viewed in the direction perpendicular to the longitudinal direction of the operator portion main body 72, and has cutouts 85 formed in the central section on the base end side. In addition, a pair of inclined surfaces 86 are formed so as to hold the cutouts 85 therebetween. A slit 87 is formed extending in the longitudinal direction by the cutouts 85 and the space interval formed by inclined surfaces 86. As shown in FIG. 9, the pair of the second expanded diameter sections 82 are formed with the hole 25A therebetween, and are each formed to utilize the through holes 88 which respectively penetrate from the operator portion main body 72 to the hole 25A. The inclined surfaces 85 are inclined so that the base end side opens. A specific interval of space is maintained between the distal end of the inclined surfaces 85 and the wall surfaces 88A on the distal end side of the through hole 88. The wall surfaces 88A form a vertical surface which is approximately perpendicular to the longitudinal direction.

Figure 10:
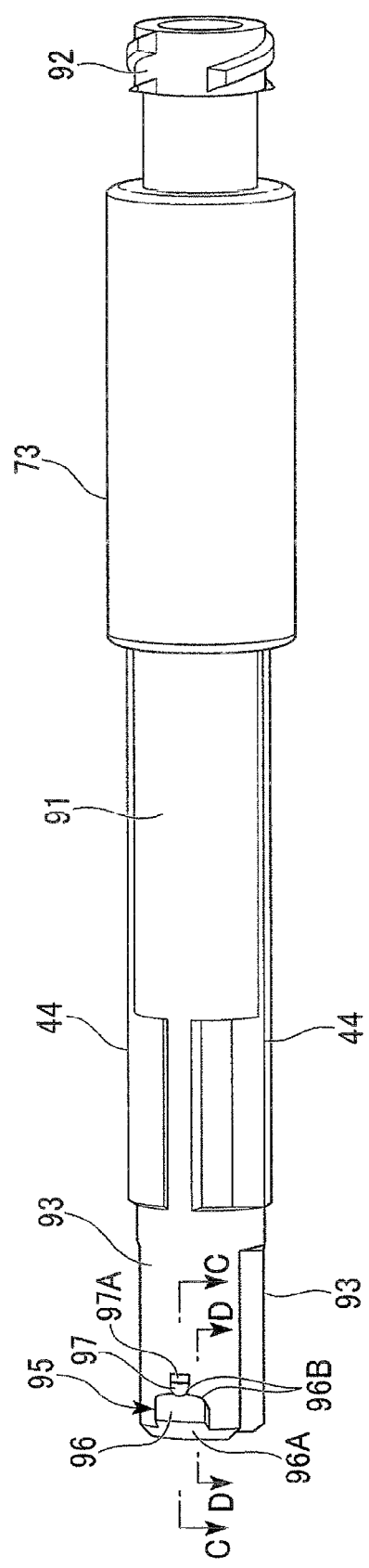
FIG. 10 is a perspective view of the operator tube.
Figure 11:
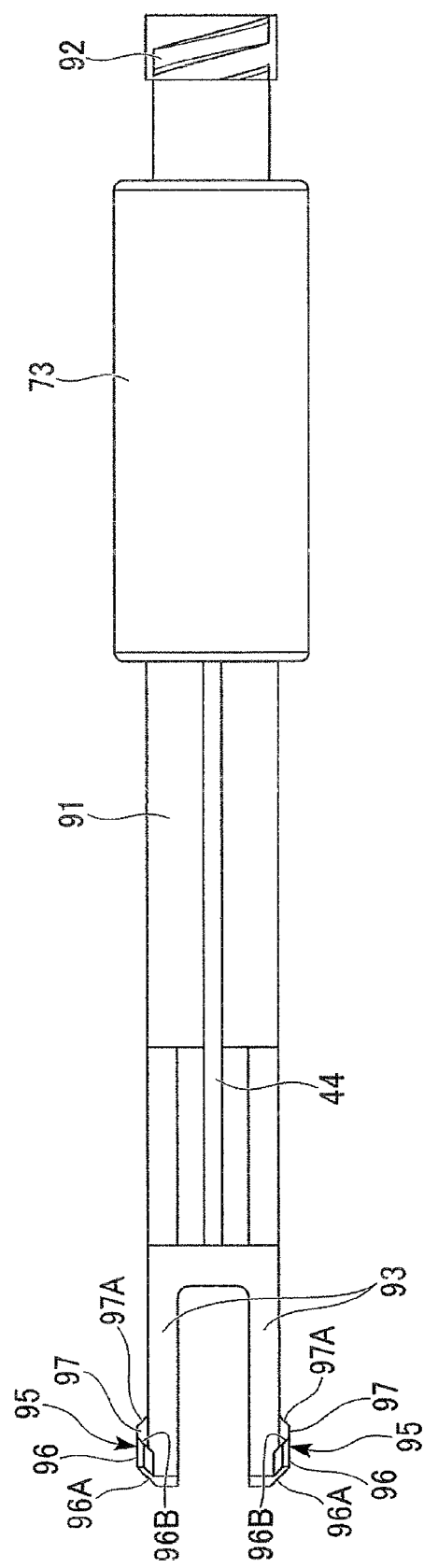
FIG. 11 is a side view of the operator tube.
Figure 12:
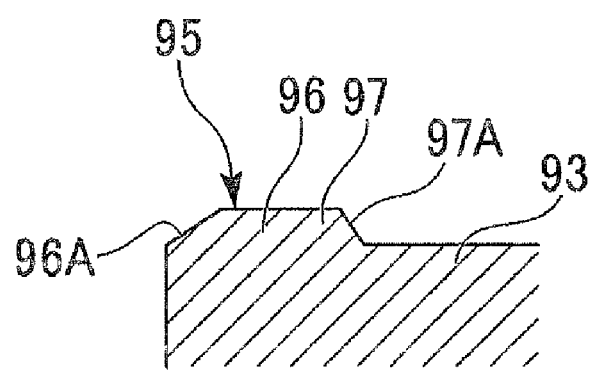
FIG. 12 is a cross-sectional view along the line C-C in FIG. 10.
Figure 13:
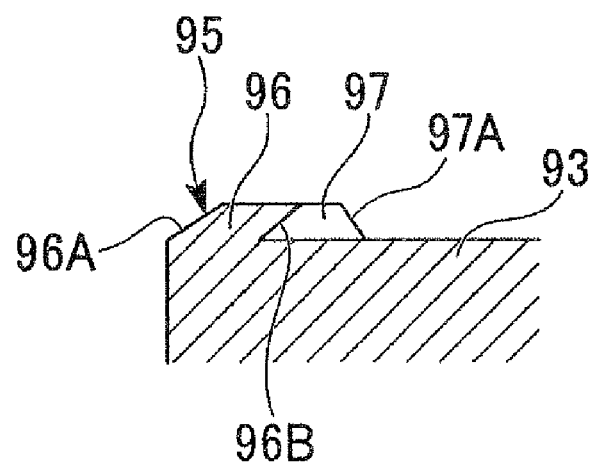
FIG. 13 is a cross-sectional view along the line D-D in FIG. 10.

As shown in FIGS. 10 and 11, the operator tube 73 is formed in a unitary manner with the base 92 on the base end of the tube portion 91, and supplies a medicinal liquid or the like to the hollow needle 4 via a through hole not shown in the figures. Keys 44 are formed corresponding to the key grooves 27 on the lateral surface of the tube portion 91. Using a slot, a pair of locking parts 93 are formed to the distal end portion of the tube portion 91. Furthermore, a pipe 42 (not shown in FIGS. 10 and 11) extends from between the pair of locking parts 93 and is connected to the liquid relaying tube 13.

The locking parts 93 are deformable in the radial direction, with the distal end side being a free end. A projecting part 95 is provided to the outside of the respective locking parts 93 in the radial direction.

The projecting part 95 has a convex shape in which the edge portion 97 projects out from the central portion on the base end side of the rectangular projecting part main body 96 as seen from the radial direction. The distal end surface of the projecting part main body 96 forms an inclined surface 96A which opens toward the base end side. The edge portion 97 extends along the longitudinal direction, and the end surface 97A on the base end side thereof forms an inclined surface which closes toward the base end. The base end surface of the projecting part main body 96 corresponding to the dropped down shoulder portion in the convex form, which is disposed so as to grip the edge portion 97, forms inclined surface 96B. The inclined surface 96B is disposed further toward the distal end side than the end surface 97A if the edge portion 97, and is a flat surface which is inclined in the direction opposite end surface 97A, i.e., inclined in the direction which closes toward the distal end.

Projecting part 95 has an outer shape which permits advance to the first and second expanded diameter sections 81,82 on the operator portion main body 72 side. The length of edge portion 97 in the longitudinal direction extending from the projecting portion main body 96 is less than the length of the slit 87 of the second expanded diameter section 82. The width in the direction which intersects with the longitudinal direction of the edge portion 97 is less than the width of the slit 87.

Figure 14:
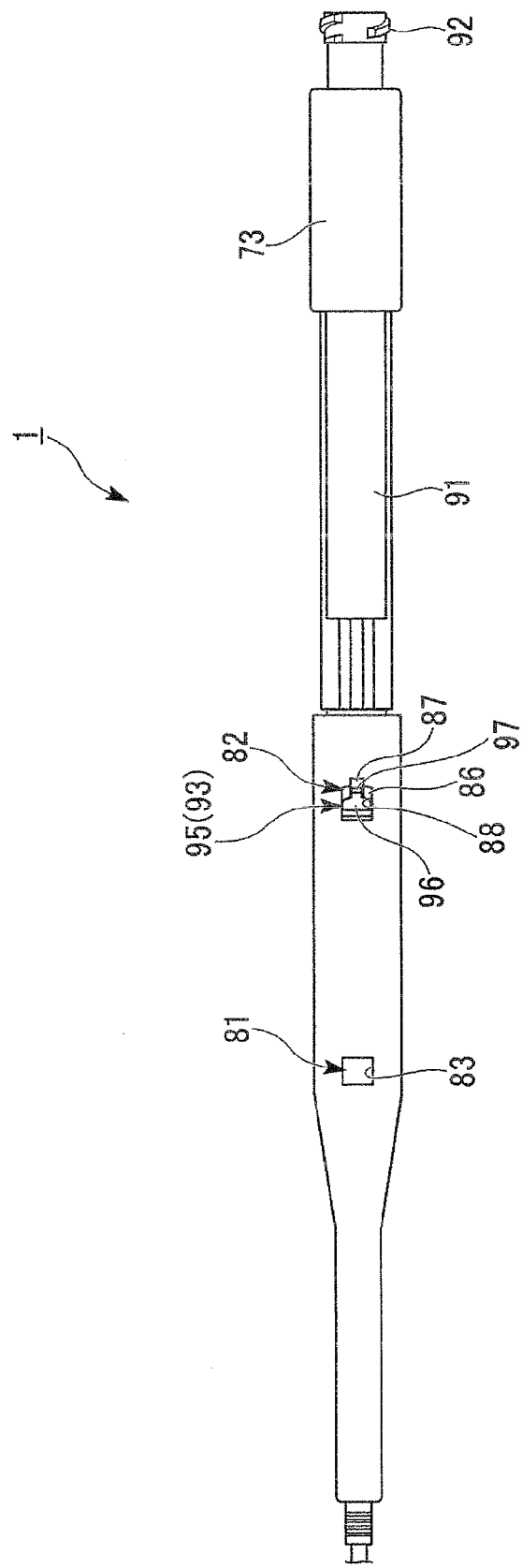
FIG. 14 is a view showing the operator tube pulled out from the state shown in FIG. 8.

The injection syringe 1 can be positioned at either the operating position or the housing position at which the hollow needle 4 is housed in the sheath 3. When inserting the injection syringe 1 into the body, the hollow needle 4 is housed at the housing position. The operator tube 73 is pulled with respect to the operator portion main body 72 at this time, engaging and stopping the locking parts 93 in the second expanded diameter section 82. As shown in FIG. 14, the projecting part main body 96 advances into the hole 88, and the edge portion 97 is housed inside the slit 87. Since the direction of inclination for the inclined surface 96B at the base end side of the projecting part main body 96 and the inclined surface 86 of the second expanded diameter section 82 is set so that there is engagement in the direction in which the operator tube 73 is pulled out, it is not possible to pull the operator tube 73 out beyond this point.

The operator tube 73 is pushed into the operator portion main body 72 when moving the hollow needle 4 from the housing position to the operating position. In contrast to the roughly vertical alignment of the wall surface 88A of the second expanded diameter section 82, the inclined surface 96A on the distal end side of the projecting part main body 96 is inclined so as to close toward the distal end. As a result, the projecting part 95 is pressed in the direction of decreasing diameter as the operator tube 73 is pushed in, causing the pair of locking parts 93 to deform in the direction of decreased diameter. When the locking parts 93 are deformed to the point that the distance between the projecting parts 95 is less than the outer diameter of the hole 25A, the operator tube 73 advances along the hole 25A. For this reason, it is possible to release the lock with relatively light force. Note that the inclined surface 96B on the base end side of the projecting part main body 96 does not engage in this direction, so that the movement of the operator tube 73 is not hindered.

When the projecting part 95 is moved to the first expanded diameter section 81, the pair of locking parts 93 are restored due to elastic force, and the entirety of the projecting part 95 including the edge portion 97 advances into the hole 83 of the first expanded diameter section 81. This position corresponds to the operating position of the hollow needle 4, and operator tube 73 and hollow needle 4 are locked at this position.

The operator tube 73 is pulled when returning the hollow needle 4 to the housing position after completion of the treatment. In contrast to the roughly vertical alignment of the wall surface 83B of the first expanded diameter section 81, the inclined surface 97A on the edge portion 97 is inclined so as to close toward the base end. As a result, the projecting part 95 is pressed in the direction of decreasing diameter as the operator tube 73 is pulled back, causing the pair of locking parts 93 to deform in the direction of decreased diameter. When the locking parts 93 are deformed to the point that the distance between the projecting parts 95 is less than the outer diameter of the hole 25A, the operator tube 73 advances along the hole 25A. The inclined surface 96B on either end gripping the edge portion 97 is disposed further toward the distal end side than the end surface 97A, so that the inclined surface 96B does not interfere with the wall surface 83B of the expanded diameter section 81. For this reason, it is possible to release the lock with relatively light force. When the projecting part 95 is moved to the second expanded diameter section 82, the locking parts 93 engage with the second expanded diameter section 82 and the position of the operator tube 73 and the hollow needle 4 are locked.

In this embodiment, the edge portion 97 is provided inclining toward the projecting parts 95 of the locking parts 93, with the locking parts 93 designed so as to deform in the reduced diameter direction during retraction of the hollow needle 4 through the cooperative action of the first expanded diameter section 81 and the end surface 97A of the edge portion 97. As a result, the lock on the operator tube 73 can be released with light force.

An inclined surface 96A is provided to the distal end of the projecting part 95 of the locking parts 93, with the locking parts 93 designed so as to deform in the reduced diameter direction during advance of the hollow needle 4 through the cooperative action of the second expanded diameter section 82 and the inclined surface 96A. As a result, the lock on the operator tube 73 can be released with light force.

Further, when the operator tube 73 is locked with the second expanded diameter section 82, the inclined surface 96B on the projecting part 95 side and the inclined surface 86 of the second expanded diameter section 82 engage in the direction of further pulling out of the operator tube 73, so that falling out of the operator tube 73 is prevented. In this case, a slit 87 for receiving edge portion 97 is provided so that edge portion 97 does not interfere with operator portion main body 72.

The present invention is not limited to the preceding embodiments, but rather can be widely applied.

For example, first expanded diameter sections 31, 61, 81, second expanded diameter sections 32, 62, 82, and locking parts 51, 65, 93 were provided as respective pairs. However, it is also acceptable to provide one each, or three or more, thereof.

The expanded diameter sections 31, 32, 61, 62, 81, 82 need not be a hole penetrating through the outer peripheral surface. A concave section formed from hole 25A in the reduced diameter direction is also acceptable.

The inclined surfaces 32A, 32B, 35A, 35B, 52A, 66A, 66B, 86, 96A, 96B, 97A may have an optional shape, such as a flat or curved surface.

In the first embodiment, it is acceptable not to provide the inclined surface 52A on the locking parts 51 side, but to form a surface which is approximately perpendicular to the axis. The flat surface 52B on the base end side of the locking parts 51 side may be in the form of an inclined surface. In the case where forming an inclined surface, the base end is inclined toward the axis in the closing orientation, in the direction of retraction.

In the third embodiment, the distal end surface of the projecting part 95 may be in the form of a perpendicular surface. In this case, the wall surface on the distal end side of the second expanded diameter section 82 forms an inclined surface so as to close toward the distal end.

In the third embodiment, the projecting part 95 had a concave shape projecting toward the base end side. However, a convex shape is also acceptable. When the indented portion of the concave shape is an inclined surface having the same orientation as the inclined surface 96B, the second expanded diameter section 82 aligns with the outer profile of the projecting part 95, and projects toward the central portion on the base end side, forming an inclined surface in this area which has the same orientation as the inclined surface 86. When the indented portion of the concave shape is an inclined surface having the same orientation as the end surface 97A, the central portion on the base end side of the first expanded diameter section 81 is projected outward, aligning with the outer profile of the projecting part 95.

The endoscope treatment tool is not limited to the injection syringe described in the embodiments herein. Rather, any design is acceptable, provided it is one in which the treatment part, such as a snare, clip or high frequency knife, for carrying out a specific treatment on the tissue is provided so as to be freely projecting and retracting.

The invention claimed is:

1. A treatment tool comprising:
an inserted part that is to be disposed inside a body, wherein the inserted part can be inserted and passed through an endoscope, wherein a treatment part for carrying out a specific treatment on a tissue is provided to a distal end of said inserted part, wherein the treatment part is configured to freely project and retract in the inserted part;
an operator portion attached to a base end portion of said inserted part which is configured to be pulled out from said endoscope, for manipulating the projection and retraction of said treatment part, said operator portion which is provided with an operator portion main body which is fixed to a sheath of said inserted part; and
an operator tube which is inserted in a freely advancing and retreating manner into a hole formed in said operator portion main body, and in which a base is provided that communicates with said treatment part; wherein,
expanded diameter sections which are formed with said hole of said operator portion main body at two sites along the advancing/retreating direction of said operator tube, a first expanded diameter section on a base end side of said hole being formed corresponding to a position at which said treatment part is housed in said sheath, and a second expanded diameter section on a distal end side of said hole being formed corresponding to a position at which said treatment part is projected out from said sheath;
locking parts which undergo deformation in the radial direction of the operator portion main body to engage with said first and second expanded diameter sections, provided to said operator tube; and
wherein said locking parts have projecting parts capable of engaging with said first and second expanded diameter sections, said projecting parts which have: an inclined end surface provided on a base end side of said projecting parts, and configured to deform said locking parts in a reduced diameter direction during retraction of said operator tube; and a first inclined surface provided to a position deviated in a circumferential direction of said operator tube with respect to said end surface, and inclined so as to close an axis of said operator tube toward a distal end of said operator tube, and said first expanded diameter section provided on the base end side of said operator portion main body has a surface provided on a based end side of an inner wall of said first expanded diameter section, and inclined so as to close said axis toward a distal end of said operator portion main body, and configured to engage with said first inclined surface.

2. The treatment tool according to claim 1, wherein
a center portion of said projecting part, which is centrally-located on a base end side of said projecting part of said locking parts, extends in the advancing/retracting direction, and said end surface is formed to this center portion;
said first inclined surface is disposed so as to grip either side with said center portion along the circumferential direction; and
a slit capable of receiving said center portion of said projecting part is provided to said base end side of said first expanded diameter section.

3. The treatment tool according to claim 1, wherein
a second inclined surface is formed to said second expanded diameter section on the distal end side, and configured to apply a pushing pressure to said locking parts so as to close said locking parts when said operator tube is retracted, and
a third inclined surface is formed to said first expanded diameter section on the base end side, and configured to apply a pushing pressure to said locking parts so as to close said locking parts when said operator tube is advanced.

4. The treatment tool according to claim 1, wherein a second inclined surface is formed on the distal end portion of said locking parts, and configured to reduce an outer profile of said locking parts toward said axial of said operator tube in the advancing direction.

* * * * *